(12) United States Patent
Bertrand et al.

(10) Patent No.: US 8,539,956 B2
(45) Date of Patent: *Sep. 24, 2013

(54) SYSTEM FOR USE WITH AN IMPLANTABLE MEDICAL DEVICE

(75) Inventors: William J Bertrand, Ventura, CA (US); Lori C Speckman, Ventura, CA (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/595,178

(22) Filed: Aug. 27, 2012

(65) Prior Publication Data

US 2013/0002243 A1    Jan. 3, 2013

Related U.S. Application Data

(60) Continuation of application No. 13/231,565, filed on Sep. 13, 2011, now Pat. No. 8,257,296, which is a division of application No. 10/698,117, filed on Oct. 31, 2003, now Pat. No. 8,015,977.

(51) Int. Cl.
*A61B 19/00* (2006.01)

(52) U.S. Cl.
USPC .................. 128/899; 600/424; 604/9

(58) Field of Classification Search
USPC ............... 128/897–899; 324/207.11–207.17, 324/207.22, 207.26, 228, 232, 233, 326, 324/329, 345, 347, 348; 604/8–10, 247, 604/248; 600/424, 44
See application file for complete search history.

(56) References Cited

U.S. PATENT DOCUMENTS

| | | | |
|---|---|---|---|
| 3,902,252 | A | 9/1975 | Farber |
| 5,136,242 | A | 8/1992 | Abraham-Fuchs |
| 5,637,083 | A | 6/1997 | Bertrand et al. |
| 5,643,194 | A | 7/1997 | Negre |
| 5,879,297 | A | 3/1999 | Haynor et al. |
| 6,129,668 | A | 10/2000 | Haynor et al. |
| 6,216,028 | B1 | 4/2001 | Haynor et al. |
| 6,263,230 | B1 | 7/2001 | Haynor et al. |
| 6,305,381 | B1 | 10/2001 | Weijand et al. |
| 2002/0022793 | A1 | 2/2002 | Bertrand et al. |
| 2005/0022403 | A1 | 2/2005 | Moskowitz et al. |
| 2005/0096579 | A1 | 5/2005 | Bertrand et al. |

FOREIGN PATENT DOCUMENTS

| | | |
|---|---|---|
| EP | 1092450 | 4/2001 |
| WO | 0054826 | 9/2000 |

*Primary Examiner* — Charles A Marmor, II
*Assistant Examiner* — Carrie R Dorna
(74) *Attorney, Agent, or Firm* — Dicke, Billig & Czaja, PLLC

(57) ABSTRACT

A system for use with an implantable flow control device having an adjustable valve and a magnetic device coupled to the valve, the system including a locator tool and an electronic magnetic-based indicator tool. The locator tool includes a processing system and an electronic display. The indicator tool is configured to couple with the locator tool. The indicator tool includes an electronic compass module configured to detect and generate a first set of data based on an orientation of magnetic fields associated with the magnetic device as an indication of the setting of the valve and measure and generate a second set of data based on ambient background magnetic fields. The indicator tool electrically communicates the data to the locator tool. The processing system receives and uses the first and second sets of data generated from the electronic compass module to determine orientation of the magnetic device.

20 Claims, 10 Drawing Sheets

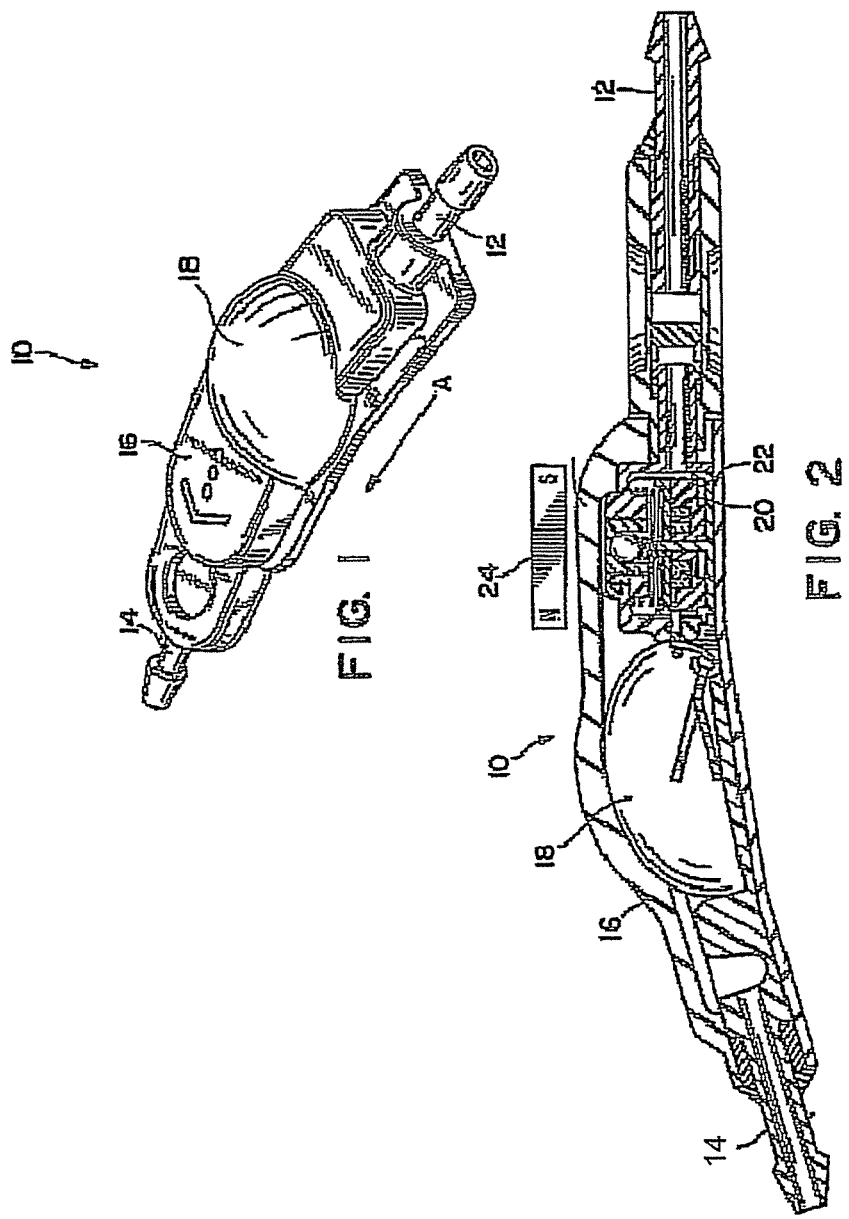

SYSTEM FOR USE WITH AN IMPLANTABLE MEDICAL DEVICE

CROSS REFERENCE TO RELATED APPLICATION

This application is a continuation of U.S. application Ser. No. 13/231,565, filed on Sep. 13, 2011, entitled "System Including an Implantable Medical Device and Electronic Valve Indicator and Locator Device", which is a division of U.S. application Ser. No. 10/698,117, filed on Oct. 31, 2003 and now U.S. Pat. No. 8,015,977, and entitled "Indicator Tool For Use With an Implantable Medical Device," which is incorporated herein by reference.

FIELD OF THE INVENTION

The invention relates to medical devices and, more particularly, to magnetic based indicator tools.

BACKGROUND

Magnetic-based indicator tools are used to determine a setting of an implantable medical device. The implantable medical device may include a fluid flow control valve that controls the pressure of cerebral spinal fluid (CSF) in a patient's brain. Excessive accumulation of cerebral spinal fluid (CSF), due to hydrocephalus or other causes, manifests itself as increased pressure within the brain. Relieving the CSF pressure is therapeutically beneficial and is usually done by using a fluid flow control valve to drain CSF from ventricles in the brain.

The implantable medical device may include a target in the form of a magnet. The magnet allows a tool set to determine the setting of the medical device and change the setting without removing the subcutaneously implanted device. The tool set typically includes a locator tool to determine the orientation of the medical device, the magnetic-based indicator tool to determine the setting of the implantable medical device by using a compass, and an adjustment tool to change the setting of the medical device by using another magnet. The tool set works by using magnetic coupling between the magnet on the implantable medical device and each of the indicator tool compass and the adjustment tool magnet.

Prior magnetic-based indicator tool relies on an interaction between the magnet on the medical device and a compass on the indicator tool that is strong enough to determine the position of the magnet even through a patient's scalp. The magnet-compass interaction must also be resistant to external magnetic fields, especially from the earth. The compass will drift toward aligning with the earth's magnetic field if the pull of the magnet in the implanted medical device is not strong enough. The deflection angle increases as the distance between the magnet and the compass increases, and may lead to inaccurate device setting indications.

Alternatively, magnetic based location tools have been developed to determine the three-dimensional location of magnetic devices within implanted medical devices. These alternate location systems typically do not attempt to determine the orientation of the magnetic devices in question and do not relate to the rotatable orientation of devices that are part of implantable valve devices. In addition, magnetic based location tools that are capable of determining the location and orientation of implanted magnetic devices are significantly more complicated in the operations performed than compass-based tools, and as such, are significantly more expensive.

U.S. Published patent application No. 2002/0022793 to Bertrand et al. discloses a compass-based indicator for assessing the position of a fluid flow valve within an implanted device. The fluid flow valve described by Bertrand et al. may be used for controlling the flow of cerebral spinal fluid (CSF) in a patient with hydrocephalus. This compass-based indicator is used in combination with an implantable flow control device disclosed within U.S. Pat. No. 5,637,083 to Bertrand et al. U.S. Pat. No. 5,879,297 and U.S. Pat. No. 6,129,668 to Haynor et al. discloses an electronic device to determine the location of a magnet coupled to an indwelling medical device using a plurality of magnetic sensors. Table 1 below lists documents that disclose devices for determining the location and orientation of magnetic devices within implantable medical devices.

TABLE 1

| Pat. No. | Inventors | Title |
| --- | --- | --- |
| U.S. Pat. No. 5,637,083 | Bertrand et al. | Implantable Adjustable Fluid Flow Control Valve |
| 2002/0022793 | Bertrand et al. | Tool for adjusting an implantable adjustable fluid flow control valve |
| U.S. Pat. No. 5,879,297 | Haynor et al. | System and method to determine the location and orientation of an indwelling medical device |
| U.S. Pat. No. 6,129,668 | Haynor et al. | System and method to determine the location and orientation of an indwelling medical device |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the structures and techniques of the present invention.

An example of a fluid control device is shown in U.S. Pat. No. 5,637,083 issued to William J. Bertrand and David A. Watson on Jun. 10, 1997 entitled "Implantable Adjustable Fluid Flow Control Valve," the teaching of which is incorporated herein in its entirety by reference. The valve of the '083 patent is shown in FIGS. 1-2 generally labeled 10 (20). (Reference numbers in parentheses correspond to the reference numbers in the '083 patent. After the corresponding reference number to the '083 patent has been given once, no further reference to the '083 will be given although the connection to the '083 patent is intended to be implied throughout this description.) The valve 10 includes an inlet connector 12 (22) and an outlet connector 14 (24). An elastomeric casing 16 (30) covers the inner workings of the valve 10. A dome 18 (60) extends upward from the elastomeric casing 16. Fluid flows through the valve 10 in the direction indicated by the arrow "A."

Valve 10 includes a mechanism to control fluid flow through the valve 10. The mechanism includes a magnet 20 (120) embedded within a base 22 (122). Rotating the base 22 changes the internal configuration of the mechanism. Changing the internal configuration of the mechanism produces a variety of pressure or flow characteristics for the valve. The base 22 may be rotated by magnetically coupling an external magnet 24 (140) to the valve's magnet 20 and rotating the external magnet 24. Because magnet 20 is coupled to the external magnet 24, when magnet 24 rotates, magnet 20 also rotates. As magnet 20 rotates, base 22 rotates and the internal configuration of the mechanism changes as described in detail in the '083 patent. As the internal configuration of the valve 10 changes, the pressure/flow characteristics of the valve 10 change. In use, the valve 10 is subcutaneously placed on the patient's skull. The catheter going to the patient's ventricle is attached to inlet connector 12. The catheter going to the patient's peritoneal cavity or vascular system is attached to outlet connector 14. In this way, a direction of flow is established from the inlet connector 12 through the valve 10 to the outlet connector 14. As stated above and described in detail in the '083 patent, changing the internal configuration of the mechanism by coupling the external magnet to the internal magnet and rotating the base produces a variety of pressure or flow characteristics through the valve 10.

SUMMARY

In general, the invention is directed to an electronic device for determining a setting for a valve that is part of an implanted flow control device. The electronic device determines the orientation of a magnetic device coupled to implantable medical devices using a magnetic-based indicator tool that interacts with an implanted medical device to assess a setting associated with the device. The invention has certain objects. That is, various embodiments of the present invention provide solutions to one or more problems existing in the prior art with respect to the magnetic-based indicator tools for interaction with implanted medical devices.

The problems include, for example, inaccuracies in the setting indication provided by a compass-based indicator tool due to the effects of external magnetic fields. The compass-based indicator tool interacts with a magnetic target that creates an internal magnetic field, and causes the compass to indicate a particular position. The position of the compass is indicative of the setting of the implantable medical device, e.g., the position of a fluid flow valve. External magnetic fields, and especially the earth's magnetic field, may interfere with the compass and create an incorrect device setting indication.

Various embodiments of the present invention have the object of solving the foregoing problems. For example, it is an object of the present invention to overcome at least some of the disadvantages of the foregoing procedures by providing a electronic-based indicator tool that produces more accurate and reliable indications of implantable device settings. To that end, it is a further object of the present invention to reduce the effects of an external magnetic field on the electronic-based indicator tool, and thereby enhance the accuracy of the tool. It is another object of the invention to reduce the effects of an external magnetic field by electronically measuring and compensating for the presence of the external magnetic field. The invention is also capable of sensing the implanted magnet at a greater distance (such as in the case where there is thick skin or scalp tissue over the implanted device) than the prior compass-based tool.

Various embodiments of the invention may possess one or more features capable of fulfilling the above objects. In general, the invention is directed to an electronic magnetic-based indicator tool that includes an electronic compass module and a processing system that uses data generated from the compass module to determine a orientation of a magnetic indication device. The magnetic indication device, being coupled to a valve used to control operation on an implantable flow control device, permits the processing module to further determine a setting for the valve from the orientation of the magnetic indication device.

In another embodiment, the invention is directed to an electronic magnetic-based indicator tool that includes a target compass module, a background compass module and a processing system that uses data generated from the compass module to determine a orientation of a magnetic indication device. The background compass module determines ambient background magnetic fields present near the indicator tool. The target compass module determines magnetic fields from both ambient background fields and magnetic fields from the magnetic indication device. The processing module subtracts the magnetic field data from the background compass module and the target compass module to determine the magnetic field generated only by the magnetic indication device. The magnetic indication device, being coupled to a valve used to control operation on an implantable flow control device, permits the processing module to further determine a setting for the valve from the orientation of the magnetic indication device.

In another embodiment, the invention is directed to a system comprising an implantable medical device that includes an implantable flow control device, an electronic magnetic-based indicator tool, and an adjustment tool. The implantable flow control device includes a magnetic device coupled to a control valve. The electronic magnetic-based indicator tool includes a compass module and a processing system that uses data generated from the compass modules to determine an orientation of a magnetic indication device. The magnetic device, being coupled to a valve used to control operation on an implantable flow control device, permits the processing module to further determine a setting for the valve from the orientation of the magnetic indication device.

In another embodiment, the invention is directed to a method which comprises placing a electronic magnetic-based indicator tool adjacent to an implantable medical device, detecting a target magnet field from a target compass module, detecting a background magnetic field from a background compass module, and indicating a device setting of the implantable medical device, wherein the device setting is indicated by the indicator tool. The target compass module and the background compass module are located distance apart sufficient to permit the background compass module to only detect ambient magnetic fields when the target compass module is located near the implanted flow control device.

In comparison to known implementations of magnetic-based indicator tools for implantable medical devices, various embodiments of the present invention may provide one or more advantages. For example, if the implantable medical device is implanted subcutaneously on a patient's skull, a magnetic-based indicator tool in accordance with the invention is capable of taking a more accurate device setting measurement through the patient's skin. As the magnetic-based indicator tool moves further away from the implantable medical device, the external magnetic fields have a greater influence on the compass. The electronic magnetic sensors compensate for an estimate of the external magnetic fields and thus preventing the corruption of the device setting measurement, even as the distance between the indicator tool and the implantable medical device increases. The electronic device is then able to indicate accurate device setting values in the cases where the patient's skin is thicker than normal. In this way, the electronic device may eliminate the need for x-rays to determine an implantable medical device setting through a surface, such as a patient's skin.

It is a primary object of the present invention to provide an improvement to accuracy of electronic magnetic-based indicator tools for use with implantable medical devices. This and other objects of the invention will become clear from an inspection of the detailed description of the invention and from the appended claims. Throughout the description, like elements are referred to by like reference numbers. An element referred to by a reference number has all the attributes and characteristics of the element as described wherever in the description unless specifically stated otherwise.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

BRIEF DESCRIPTION OF DRAWINGS

FIG. 1 is a schematic diagram illustrating a subcutaneously implantable and adjustable fluid flow control device for use with an improved valve indicator tool device according to an example embodiment of the present invention.

FIG. 2 is a cross-sectional diagram further illustrating the adjustable fluid flow control device of FIG. 1.

DETAILED DESCRIPTION OF THE PREFERRED EMBODIMENTS

Figure 3:
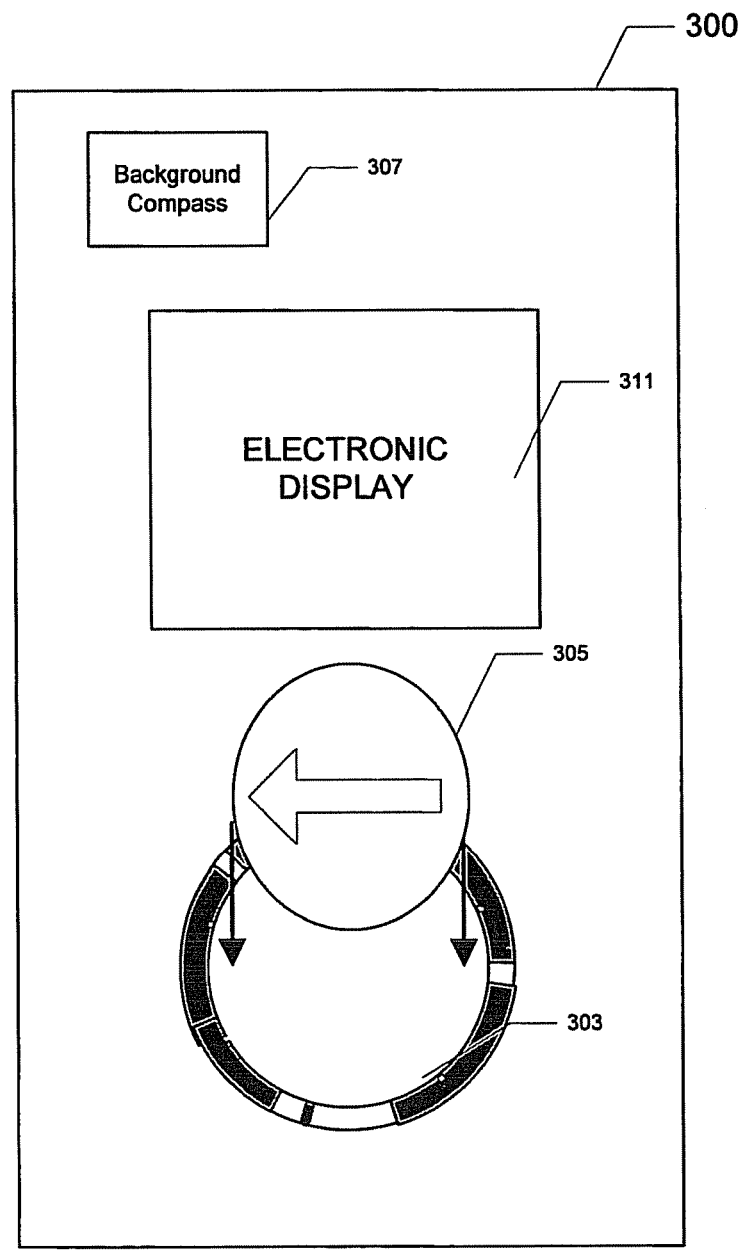
FIG. 3 is a schematic diagram illustrating an improved electronic valve indicator and locator tool in accordance with an example embodiment of the present invention.

As shown in the drawings for purposes of illustration, the FIGS. 1 and 2 illustrate a subcutaneously implantable and percutaneously adjustable fluid flow control device, generally designated in the accompanying drawings by the reference numbers 10. The fluid flow control devices 10 is intended for use in a surgically implanted physiological shunt system for draining fluid from one portion of the body to another. In order to connect, for example, the device 10 in such a system, the device includes an inlet connector 12 and an outlet connector 14 which each receive one end of a piece of surgical tubing (not shown). The ends of the surgical tubing are placed over the connectors 12 and 14 and secured thereon by a single ligature just inside of an annular ridge formed near the end of each connector.

When the flow control device 10 is used in a drainage system intended for the treatment of hydrocephalus, the inlet connector 12 is fluidly connected with a proximal catheter which is inserted through the skull into a brain ventricle containing cerebrospinal fluid under pressure. The outlet connector 14 is fluidly connected to a distal catheter which serves to discharge cerebrospinal fluid to, for example, the atrium portion of a patient's heart. Ordinarily the flow control device 10 will be surgically implanted on the patient's skull with a flap of skin overlying the device. To facilitate holding the device in its desired position after implantation, a generally flexible mounting plate can be provided with one or more suture holes.

The highly reliable fluid flow control device which has a single flow path there through and a valve mechanism which can be percutaneously adjusted when the device is subcutaneously implanted by the use of the present invention. The flow control device 10 include a relatively rigid, molded plastic base invested within an electrometric casing which, together, define a fluid flow path through the fluid flow control devices from the inlet connector 12 to the outlet connector 14. The valve housing includes a percutaneously adjustable valve mechanism which restricts the flow of fluid through the device 10. Coupled to the adjustable valve mechanism is a magnetic indication device that may be externally located using an indicator tool. The present invention provides an improved mechanism for determining the setting the adjustable valve mechanism. The flow control device is described in more detail in U.S. Pat. No. 5,637,083 issued to Bertrand et al. entitled "Implantable Adjustable Fluid Flow Control Valve."

FIG. 3 is a schematic diagram illustrating an improved electronic valve indicator and locator tool in accordance with an example embodiment of the present invention. In this embodiment, a locator tool 300 is shown with an indicator tool 305 being placed into position over its corresponding indicator position 303. The locator tool 300 includes an electronic display 311 to provide graphical and textual information to a user while the locator tool is in operation. The locator tool 300 also includes a background compass module 307 to measure ambient and background magnetic fields without influence from a magnetic device coupled to the implantable flow control device.

In operation, the indicator tool 305 operates as an electronic compass to detect the orientation of magnetic fields associated with the magnetic device coupled to the valve in the implanted flow control device. The orientation of the magnetic device provides an indication of the setting for the valve. The indicator tool 305 is placed into its corresponding location on the locator tool 300 once the locator tool 300 is placed near the patient at a location corresponding to the site of the implantable flow control device. Typically, the indicator tool is keyed to place the tool 305 into a pre-defined orientation relative to the locator tool 300. This keying mechanism assists in placing the indicator tool 305 directly over an implanted flow control device once the flow control device has been identified and properly oriented relative to the locator tool 300. The indicator tool 305 obtains its reading for the detected orientation of the magnetic field. This reading is communicated to the locator tool 300 for use in determining the setting for the valve.

The reading obtained from the indicator tool 305 corresponds to magnetic fields that are a combination of a magnetic field generated by the magnetic device coupled to the valve of the implanted flow control device and ambient background magnetic fields. The reading from the indicator tool 305 is then processed to subtract an estimate for the ambient background magnetic fields obtained from the background compass 307 to generate a orientation for the magnetic field generated just by the magnetic device coupled to the valve of the implanted flow control device.

The background compass 307 provides the ambient background magnetic field estimate when the background compass 307 is located within the locator tool at a position significantly separated from the expected location of the magnetic device coupled to the valve of the implanted flow control device when in place near a patient. Because the magnetic field typically observable at a distance of 12 cm from a typical magnetic indicator device coupled to an implantable flow control device is generally less than 5 milliGauss, the indicator tool must be placed as close as possible to the flow control device to permit the indicator tool to detect this magnetic field within the Earth's background magnetic field typically observed to be approximately 500 milliGauss. As such, a background compass located far enough away from the implanted flow control device will not readily detect magnetic fields from the magnetic device coupled to the valve of the implanted flow control device.

Figure 4:
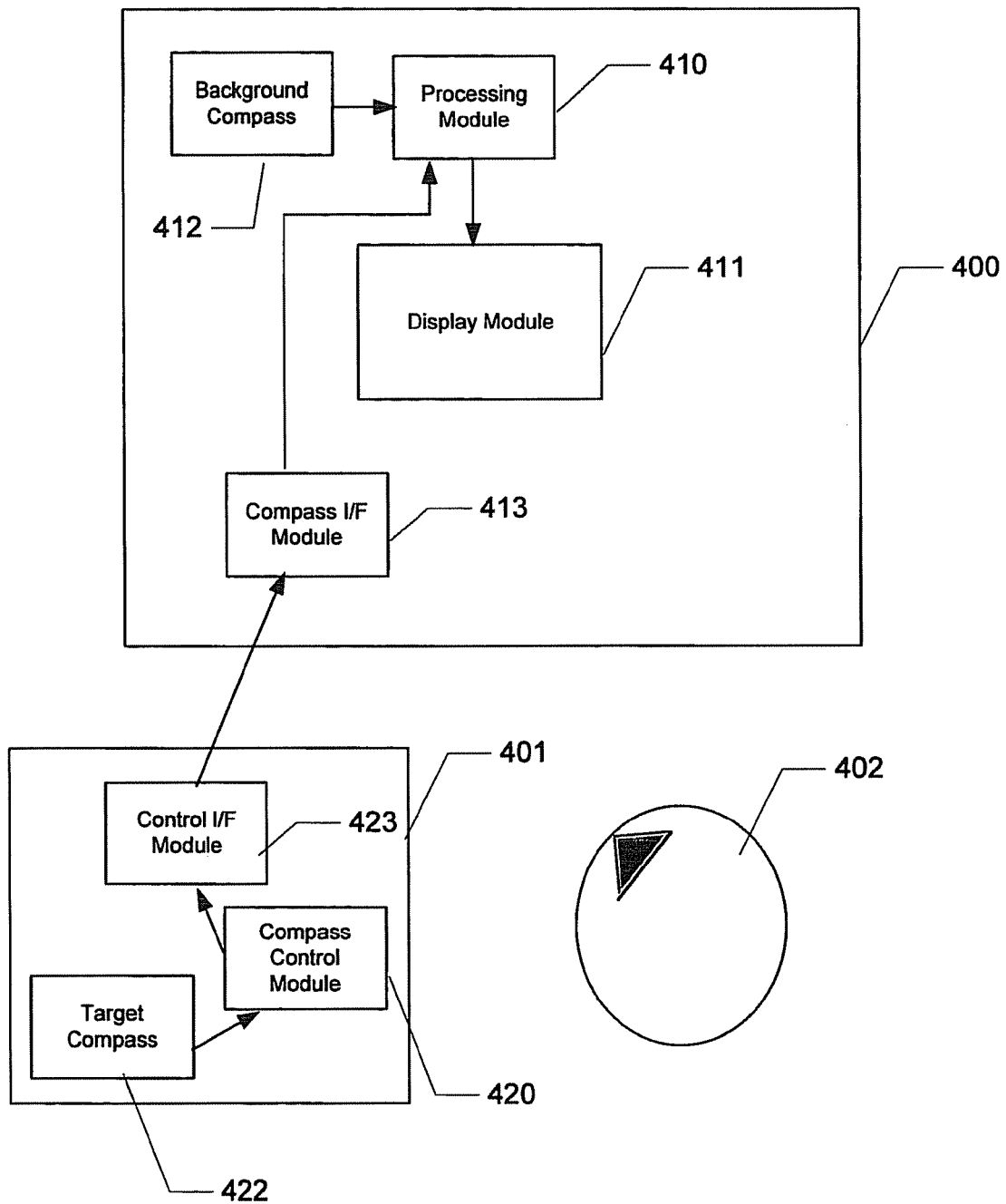
FIG. 4 is a block diagram illustrating internal electronic modules used in implementing an embodiment of the indicator and locator tool of FIG. 3.

FIG. 4 is a block diagram illustrating internal electronic modules used in implementing an embodiment of the indicator and locator tool of FIG. 3. Tool set used to determine a valve setting and modify the valve setting on an implantable flow control device typically comprises three components: a locator tool 400, an indicator tool 401, and an adjustment tool 402. The locator tool 400 typically provides a base unit that is used to locate the implanted flow control device in a patient. When the locator tool 400 is placed above the implanted flow control device near a patient, either the indicator tool 401 or the adjustment tool 402 is aligned with the locator tool 400 to orient either tool 401-402 into a proper position to perform its associated task.

The locator tool includes a set of modules to perform its functions. These modules include a display module 411, a processing module 410, a background compass module 412, and a target compass interface module 413. The display module 411 is a display device for providing a user with graphical and textual information associated with the operation of the locator tool 400. This display device 411 illustrates a setting for a valve on the implanted flow control device using the magnetic field data obtained from the background compass 412 and the indicator tool 401. The processing module 410 is a programmable processing module to perform all control and data processing functions of the locator tool as well as its communication and control functions over the operation of the indicator tool.

The background compass 412 is an electronic compass comprising one or more magnetic field detector devices used to measure the orientation of ambient background magnetic fields. As noted above, the background compass module is physically located within the locator tool 400 far enough away from the position of the indicator tool when it is in an operating position to not be affected by magnetic fields generated by magnetic device coupled to the valve of the implanted flow control device.

The compass interface module 413 provides a data communications channel between the indicator tool 401 and the modules within the locator tool 400. The indicator tool 401 provides its orientation data for use in subtracting background magnetic field data to obtain a correct valve setting. The indicator tool 401 electrically communicates this data to the locator tool 400 through a pair of interface modules. Electrically, the two interface modules are electrically coupled together. This electrical connection may be a connection cable between the locator tool 400 and the indicator tool 401. Alternately, both the locator tool 400 and the indicator tool 401 may possess electrical connectors that engage each other when the indicator tool 401 is placed into its corresponding position on the locator tool 400 once the locator tool 400 is placed above the flow control device implanted in a patient. Of course, one skilled in the art will recognize other communication mechanisms including wireless communications channels constructed using IR or RF wireless communications may be used without deviating from the spirit and scope of the present invention as recited within the attached claims.

The indicator tool 401 includes a target compass module 422, a compass control processing module 420, and a locator tool interface module 423. The target compass module 422 is an electronic compass comprising one or more magnetic field detector devices used to measure the orientation of a target magnetic field when the locator tool 400 and the indicator tool 401 are in their respective locations above an implanted flow control device. The compass control processing module 420 is a processing module used to control the operation of the indicator tool when data is collected and subsequently communicated to the locator tool 400. This processing module may comprise a programmable processing device to permit software to be developed to perform the processing tasks associated with the indicator tool 401. One skilled in the art will recognize that this processing module may also be implemented as a custom control module using a state machine or similar control logic as is typically used in embedded processing applications. The indicator tool 401 and locator tool 400 are handheld devices that may be moved to place them into positions near a patient. As such, these tools are typically powered by mobile power sources such as batteries. As such, the complexity of these processing modules is minimized to reduce the needs for power consumption of the tools while in operation to maximize the battery life before the batteries are recharged or replaced.

The locator tool interface module 423 provides an electrical interface for the communications channel described above between the locator tool 400 and the indicator tool 401. Typically this communications channel is a serial data channel that transmits data a single bit at a time as a sequence of one bit data values. The interface modules on both sides of the communications channel perform any parallel to serial and serial to parallel data transformations needed to utilize this communication channel.

The adjustment tool 402 is a magnetic device that is placed into position once the locator tool is in place. The magnetic device in the adjustment tool 402 couples to the magnet within an implanted flow control device to allow a setting for the valve to be changed as desired. The operation the adjustment tool is discussed below in more detail in regards to FIG. 8.

Figure 5:
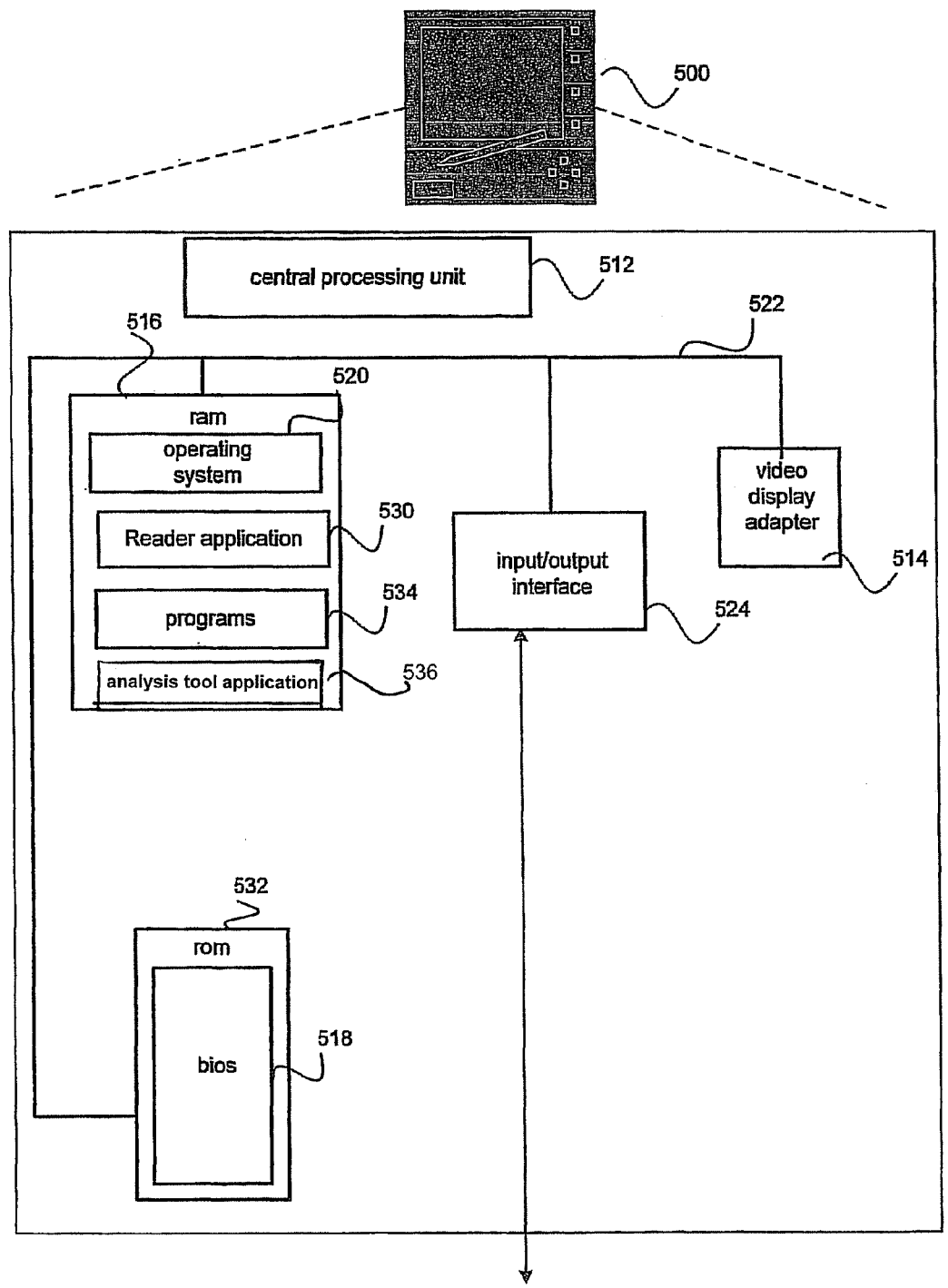
FIG. 5 is a block diagram illustrating a general programmable processing system for use in a handheld device such as an improved indicator and locator tool in accordance with an example embodiment of the present invention.

FIG. 5 is a block diagram illustrating a general programmable processing system for use in a handheld device such as an improved electronic valve indicator tool and adjustment tool in accordance with an example embodiment of the present invention. In an exemplary embodiment of a handheld processing system 500, computing system 500 is operative to provide a magnetic valve indicator tool processing system. Those of ordinary skill in the art will appreciate that the magnetic valve indicator tool 500 may include many more components than those shown with reference to a computing system 500 shown in FIG. 5. However, the components shown are sufficient to disclose an illustrative embodiment for practicing the present invention.

As shown in FIG. 5, magnetic valve indicator tool processing system 500 is used in connection with an implantable flow control device 10 as needed. The magnetic valve indicator tool processing system 500 also includes processing unit 512, video display adapter 514, and a mass memory, all connected via bus 522. The mass memory generally includes RAM 516, ROM 532, and may include one or more mass storage devices, such as a removable memory device such as a Compact Flash, Smart Media, or Secure Digital memory card. The memory devices may store an operating system 520 for controlling the operation of magnetic valve indicator tool processing system 500. It will be appreciated that this component may comprise a general purpose server operating system as is known to those of ordinary skill in the art, such as UNIX, MAC OS™, LiNUX™, or Microsoft WINDOWS®. Basic input/output system ("BIOS") 518 is also provided for controlling the low-level operation of processing system 500.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. The mass memory also stores program code and data for providing a software development and neural network analysis and training system. More specifically, the mass memory stores applications including magnetic valve indicator tool program 530, and other programs 534, and similar analysis tool applications 536 as may be needed. The magnetic valve indicator tool processing program 530 includes computer executable instructions which are executed to perform the logic described herein.

The magnetic valve indicator tool processing system 500 also comprises input/output interface 524 for communicating with external devices, such as a touch screen and similar input devices, or other input devices not shown in FIG. 5. Likewise, The magnetic valve indicator tool processing system 500 may further comprise additional mass storage facilities also not shown should additional data storage be needed.

One skilled in the art will recognize that the processing system illustrated within FIG. 5 may represent a set of processing components typically found within a handheld or similar dedicated processing system. Of course, other processing systems including general purpose computing systems containing additional peripherals and user interface devices may also be used to implement the programmable processing according to various embodiments of the present invention without deviating from the spirit and scope of the present invention as recited within the attached claims. For example, a dedicated processing system may consist of a digital signal processor (DSP) for performing the required floating-point math, various internal memory types including FLASH, ROM, RAM, and FPGA, some minimal external memory for the valve calibration system, and a user interface and display driver chip to run the switches and custom LCD display. A proprietary embedded operating system is and a specifically written application for implementing the indicator tool program may be included.

FIG. 5 illustrates an example of a suitable operating environment in which the invention may be implemented. The operating environment is only one example of a suitable operating environment and is not intended to suggest any limitation as to the scope of use or functionality of the invention. Other well known computing systems, environments, and/or configurations that may be suitable for use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Processing devices typically includes at least some form of computer readable media. Computer readable media can be any available media that can be accessed by these devices. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by processing devices.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Additionally, the embodiments described herein are implemented as logical operations performed by a programmable processing device. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 6A:
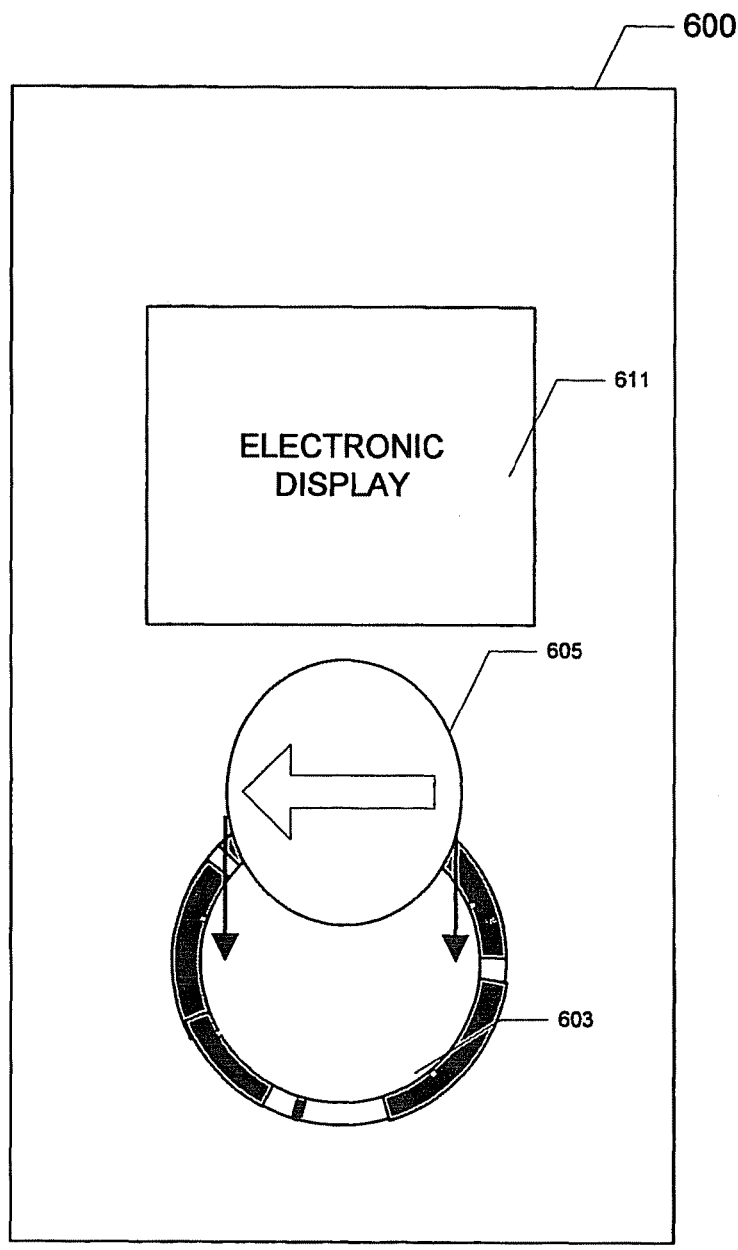
FIG. 6A is a schematic diagram illustrating an improved electronic valve indicator and locator tool in accordance with another example embodiment of the present invention.
Figure 6B:
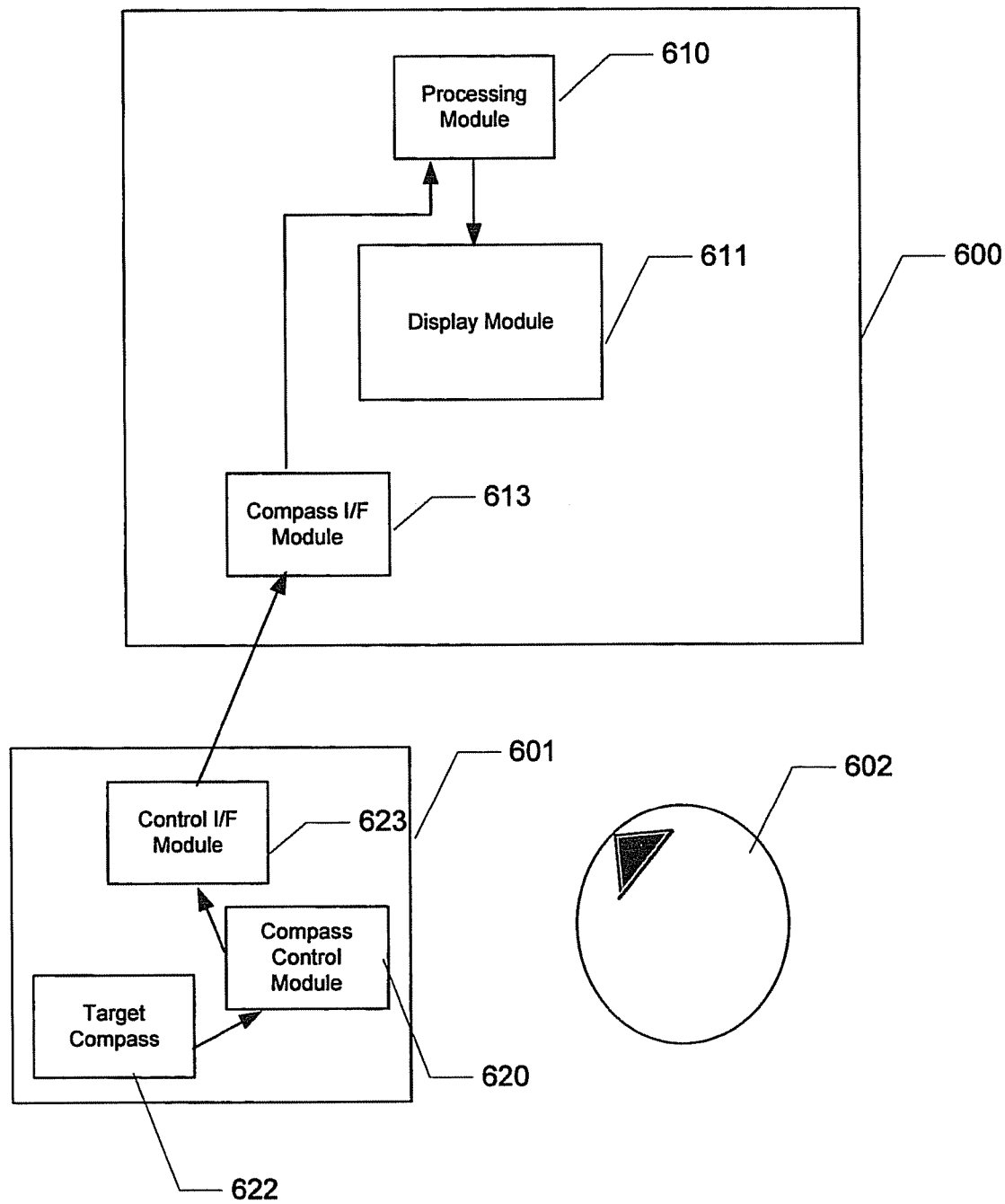
FIG. 6B is a block diagram illustrating internal electronic modules used in implementing an embodiment of the indicator and locator tool of FIG. 6A.
Figure 7A:
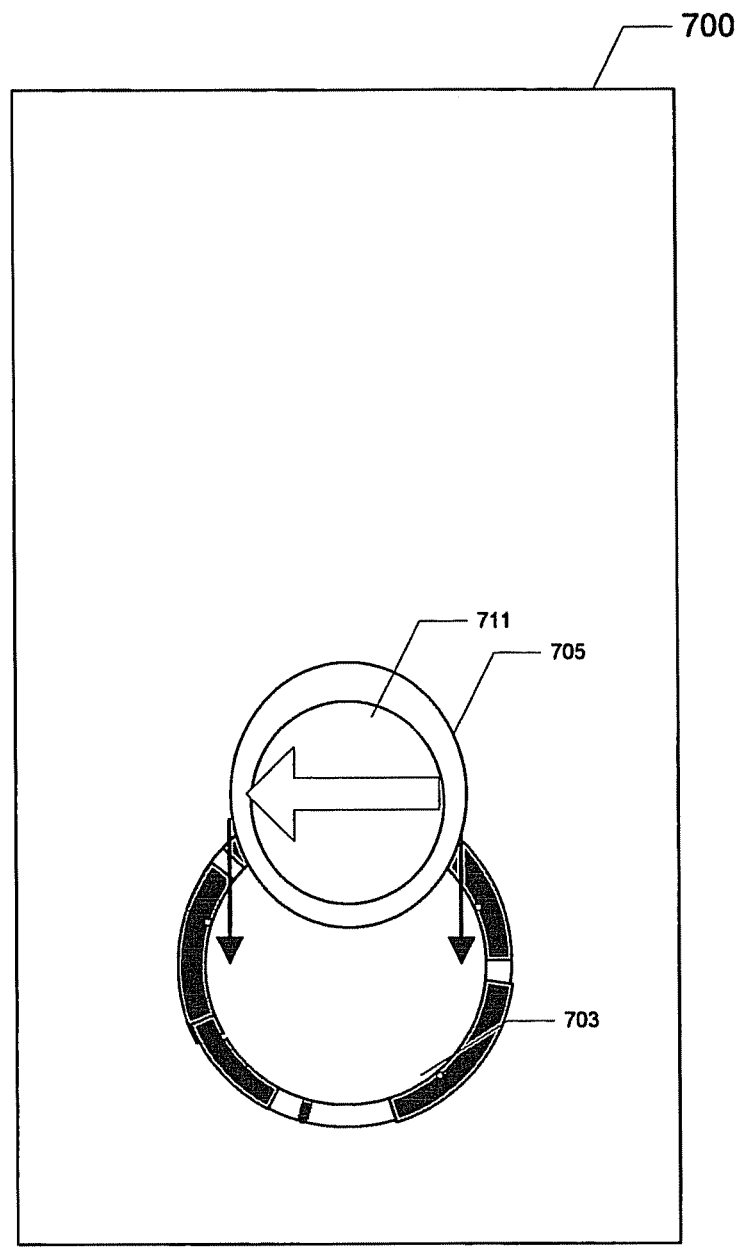
FIG. 7A is a schematic diagram illustrating an improved electronic valve indicator and adjustment tool in accordance with yet another example embodiment of the present invention.
Figure 7B:
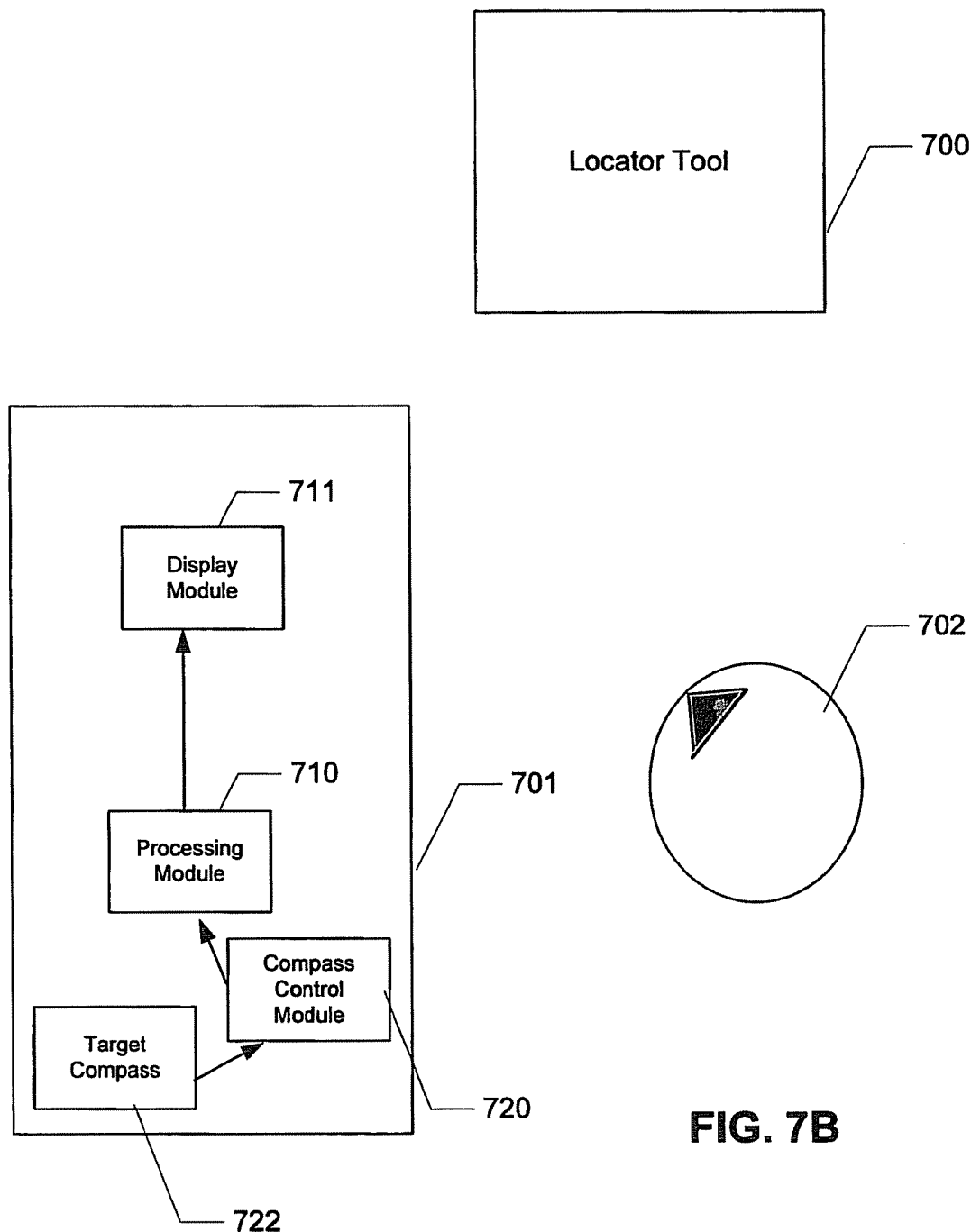
FIG. 7B is a block diagram illustrating various embodiments of internal electronic modules used in implementing an embodiment of the indicator and locator tool of FIG. 7A.

FIG. 6A is a schematic diagram illustrating an improved electronic valve indicator and locator tool in accordance with another example embodiment of the present invention. FIG. 6B is a block diagram illustrating internal electronic modules used in implementing an embodiment of the indicator and locator tool of FIG. 6A. In this embodiment, the three piece locator, indicator and adjustment tool set operate in the same manner as discussed above with respect to FIGS. 3 and 4 respectively except that this embodiment does not include a separate background compass as discussed above. Similarly, FIG. 7A is a schematic diagram illustrating an improved electronic valve indicator and adjustment tool in accordance with yet another example embodiment of the present invention. FIG. 7B is a corresponding block diagram illustrating internal electronic modules used in implementing an embodiment of the indicator and locator tool of FIG. 7A.

In the embodiment of FIG. 6A and 6B, the compass module of the indicator tool 605 is used to generate magnetic field data for both ambient background magnetic fields and target magnetic fields. The locator tool 600 is held away from a patient with the indicator tool 605 in its proper place when magnetic field data is obtained for just the ambient background magnetic fields. This data is stored within the locator tool 600. The locator tool 600 is next placed over the implanted flow control with the indicator tool 605 in place over its corresponding indicator position 603 and a second reading is obtained. The second reading corresponds to the magnetic fields that are a combination ambient background magnetic fields and target magnetic fields as discussed above. The locator tool 600 processes these two magnetic fields data values as described above to obtain the setting for the valve within the implanted flow control device.

The electronic modules within the devices as shown in FIG. 6B perform the functions described above in regards to FIG. 4. The background magnetic fields data is generated by the compass module 622 in the indicator tool 601 and transmitted to the compass control module 620 and then through the communications channel of the interface modules 613, 623 for storage within the processing module 610. Once the tools are placed over an implanted flow control device, the compass module 622 generated additional data that is again transmitted to the processing module 610. The two sets of magnetic field data is processed in the processing module 610 to generate a setting value for the valve in the flow control device and the setting data is displayed to a user on the display module 611. The adjustment tool 602 may be used as discussed below to change a setting for the valve as desired. The valve position detection process may be repeated once the valve has been adjusted to verify the new setting for the valve.

FIG. 7B is another embodiment of a block diagram illustrating internal electronic modules used in implementing an embodiment of the indicator and locator tool 705. In this embodiment, the electronics for the compass module 722, processing module 710, and display module 711 are all located within the indicator tool 701. The compass module 722 measures the magnetic fields for both the ambient background fields as well as the target magnetic field and communicates the data to the processing module 710 via the compass control module 720. Because all of these electronic modules are located within the indicator tool 705 over its corresponding indicator position 703, a communications channel and corresponding interface modules are not needed. This embodiment places the electronic display 711 from the locator tool 700 to the indicator tool 705 over its corresponding indicator position 703 as shown in FIG. 7A. The adjustment tool 702 may be used as discussed below to change a setting for the valve as desired.

The indicator tool 701, however, may need to be larger in size to contain all of these electronic modules as well as a power supply, battery, and other associated components. The indicator tool 701 would also need to nest with the housing of the locator tool 700. Such an embodiment would, however, operate with existing locator tools that do not currently include any electronics. The packaging of this compass and corresponding electronics into a small indicator tool could present the limitations of any such design. The indicator tool may be implemented in a housing that is substantially mushroom shaped. A smaller bottom portion of the indicator tool 701 may contain the magnetic compass module in order to place them close to the valve of the implantable flow control device. Such an arrangement permits the smaller bottom portion of the tool to nest within the locator tool. A larger cap part provides additional space as needed for additional electronics. One skilled in the art, however, would recognize that either embodiment works to implement the present invention as disclosed herein with the inclusion of the electronic modules within one and two tools is a matter of design choose within the scope and spirit of the present invention as recited within the attached claims.

Figure 8:
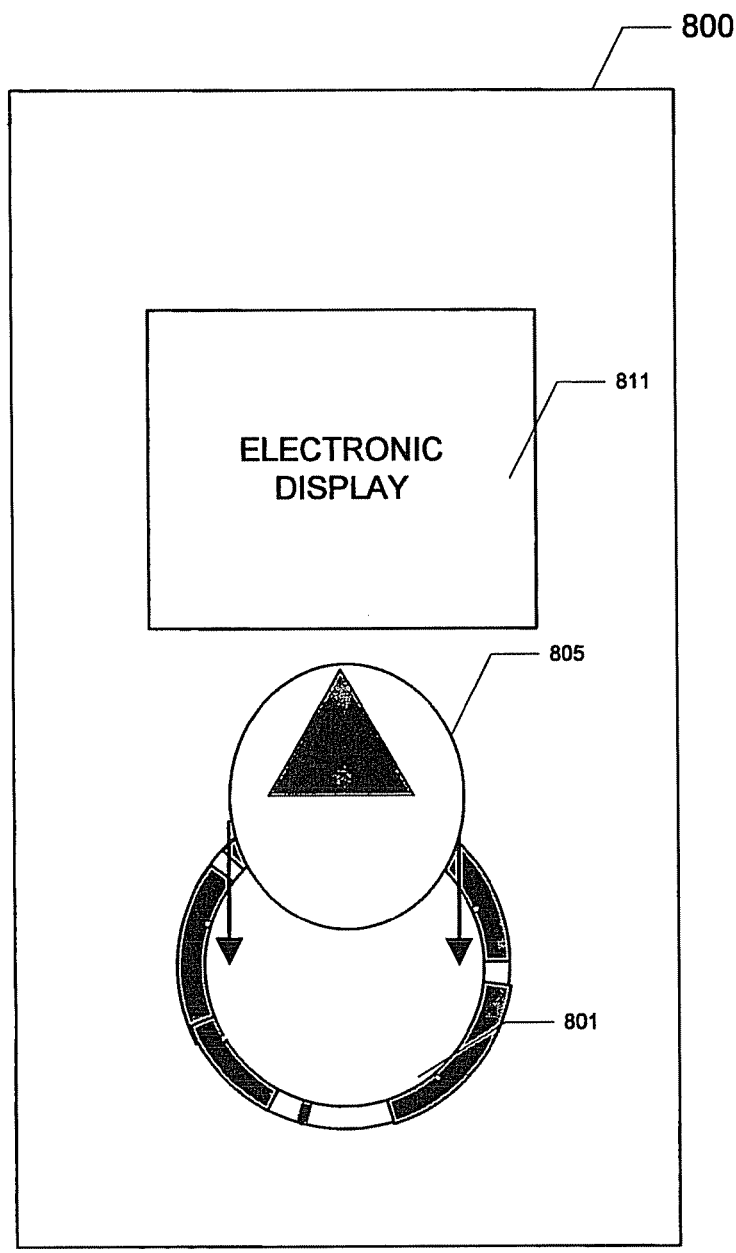
FIG. 8 illustrates a diagram of an improved electronic valve indicator tool while used with an accompanying adjustment tool in accordance with an example embodiment of the present invention.

FIG. 8 illustrates a diagram of an improved locator tool while used with an accompanying adjustment tool in accordance with an example embodiment of the present invention. Once the current position of the valve is determined and displayed on display module 811, the adjustment tool 805 may be used to alter the setting for the valve within the flow control device. The adjustment tool 805 corresponds to a magnetic coupling device that is placed over the locator tool 800 to orient the adjustment tool 805 directly over the magnetic indication device 801 that is part of the valve. The adjustment tool 805 magnetically couples to the magnetic indication device 801 such that a rotation of the adjustment tool 805 causes the magnetic indication device 801 to rotate within the valve. This rotation of the magnetic indication device 801 changes the settings for the valve within the flow control device as the magnetic indication device 801 is directly coupled to the valve setting mechanism. The operation of the adjustment tool 805 is disclosed in additional detail with the published U.S. patent application to Bertrand et al., No. 2002/0022873 as identified above.

Figure 9:
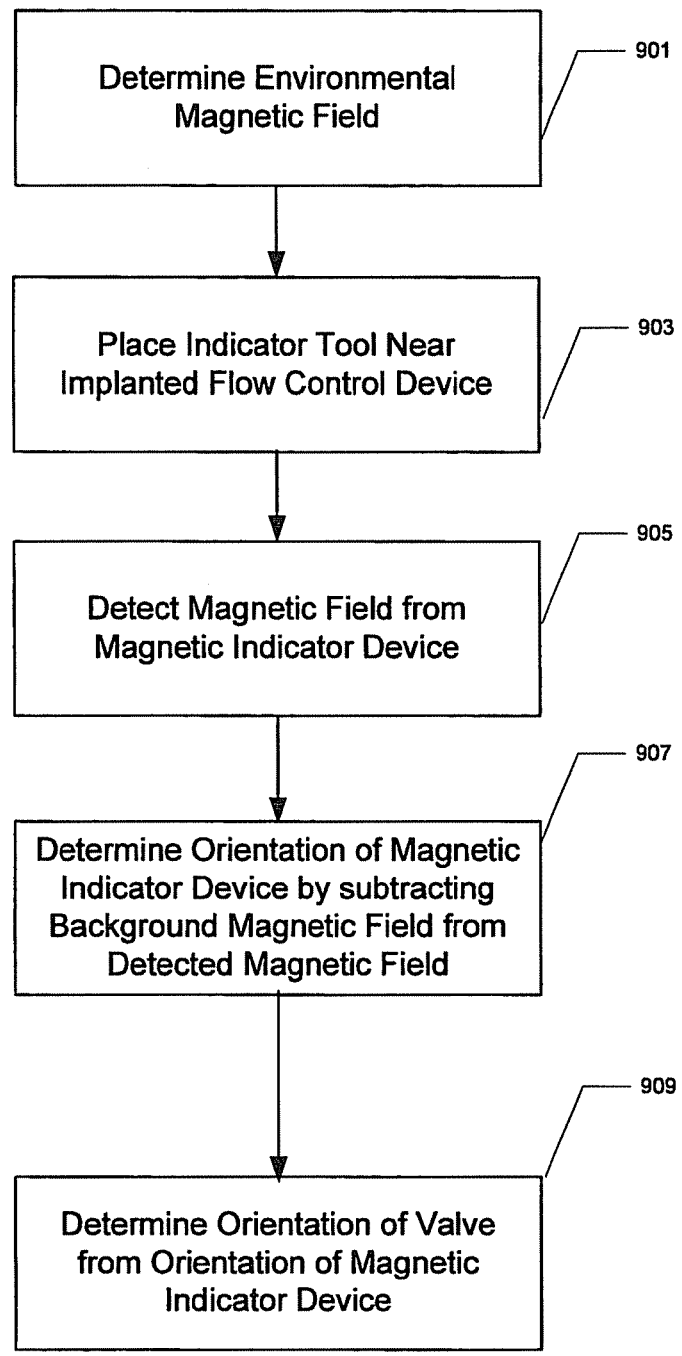
FIG. 9 illustrates a flowchart of a method for use of an improved electronic valve indicator and adjustment tool in accordance with an example embodiment of the present invention.

FIG. 9 illustrates a flowchart of a method for use of an improved indicator tool in accordance with an example embodiment of the present invention. The method for determining the setting of a valve within an implantable flow control device begins by determining an estimate for background magnetic fields 901. Next, the method for determining the setting of a valve within an implantable flow control device places the indicator tool 903 near the implantable flow control device within a patient.

Once the indicator tool is located as close to the flow control device as possible, the indicator tool detects an observed magnetic field 905 from all sources using a set of target compass module. The background magnetic fields may be subtracted from the observed values 907 to obtain a orientation for the magnetic indicator device coupled to the valve that is part of the implanted flow control device. As discussed above, the background magnetic fields may be measured using the separate a background compass module and a target compass module as well as measured using a single compass module with the indicator tool located in two positions. A method practiced using principles of the present invention may utilize either of these two device embodiments to perform the method.

The orientation of the magnetic indicator device is compared to a known orientation of the flow control device to determine a setting 909 for the valve of the flow control device. The known orientation of the flow control device may be manually determined by requiring the indicator tool to be oriented to a particular position relative to flow control device. Once the indicator tool has determined the setting for the valve, a user may utilize an adjustment tool to magnetically rotate and thus alter the setting of the valve as desired In the claims, any means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A system for use with an implantable flow control device having an adjustable valve and a magnetic device coupled to the valve to indicate a current setting of the valve, the system comprising:
   a locator tool including a processing system and an electronic display; and
   an electronic magnetic-based indicator tool configured to couple with the locator tool, the indicator tool including an electronic compass module configured to detect and generate a first set of data based on an orientation of magnetic fields associated with the magnetic device as an indication of the setting of the valve and configured to measure and generate a second set of data based on ambient background magnetic fields;
   wherein the indicator tool electrically communicates the first and second sets of data to the locator tool; and
   wherein the processing system receives and uses the first and second sets of data generated from the electronic compass module to determine orientation of the magnetic device.

2. The system of claim 1, further comprising an adjustment tool configured to magnetically couple with the indicator tool and rotate with respect to the locator tool for modifying the setting of the valve in the implantable flow control device when magnetically coupled to the implantable flow control device.

3. The system of claim 1, further comprising interface modules on the locator tool and the indicator tool configured to communicate data with each other.

4. The system of claim 1, wherein the electronic display provides a user with graphical and textual information associated with the operation of the system.

5. The system of claim 1, wherein the indicator tool further comprises a compass control module for controlling operation of the indicator tool based on the first and second sets of data.

6. The system of claim 1, wherein the indicator tool and the locator tool are handheld devices.

7. The system of claim 6, wherein the handheld devices include batteries.

8. The system of claim 1, wherein a processing module of the processing system subtracts the second set of data from the first set of data to determine the orientation of the magnetic device.

9. The system of claim 1, further comprising a key device for coupling the indicator tool into a predetermined orientation relative to the locator tool.

10. A system for determining a valve setting of an implanted adjustable flow control having an adjustable valve and a magnetic device coupled to the valve to indicate a current setting of the valve device, the system comprising:
    an electronic magnetic-based indicator tool comprising an electronic target compass configured to detect and generate a first set of data based on an orientation of magnetic fields associated with the magnetic device as an indication of the setting of the valve; and
    a locator tool configured to receive and couple with the indicator tool, the locator tool comprising an electronic background compass module configured to measure and generate a second set of data based on ambient background magnetic fields and a processing module configured to receive the first and second sets of data and to determine the valve setting based on the first and second sets of data; and
    wherein the locator tool and the indicator tool are configured to electronically communicate with each other.

11. The system of claim 10, wherein the processing module subtracts the second set of data from the first set of data to obtain the valve setting.

12. The system of claim 10, wherein the background compass module is located on the locator tool such that it does not readily detect magnetic fields from the magnetic device when aligned with the implantable flow control device.

13. The system of claim 10, wherein the locator tool further comprises a display module configured to electronically display valve setting information.

14. The system of claim 10, further comprising an adjustment tool configured to magnetically couple with the indicator tool and rotate with respect to the locator tool for modifying the valve setting of the valve in the implantable flow control device when magnetically coupled to the implantable flow control device.

15. The system of claim 10, wherein the indicator tool is keyed into a predetermined orientation relative to the locator tool.

16. The system of claim 10, wherein the target compass comprises at least one magnetic field detector device.

17. The system of claim 10, wherein the indicator tool and the locator tool are handheld devices.

18. A system for use with an implantable flow control device comprising an adjustable valve and a magnetic device coupled to the valve to indicate a current setting of the valve, the system comprising:
    a locator tool for locating an orientation of the implantable flow control device; and
    an electronic magnetic-based indicator tool configured to nest with the locator tool, the indicator tool comprising:
        an electronic compass module for measuring and generating data based on an orientation of magnetic fields associated with the magnetic device as an indication of the setting of the valve and ambient background magnetic fields;
    a processing system for receiving the data generated from the electronic compass module to determine the valve setting; and
    an electronic display for providing a user with graphical and textual information associated with the operation of the system.

19. The system of claim 18, wherein the indicator tool further comprises a compass control module for controlling operation of the indicator tool based on the data.

20. The system of claim 18, further comprising an adjustment tool for rotating the indicator tool and modifying the valve setting of the valve in the implantable flow control device when magnetically coupled to the implantable flow control device.

* * * * *